(12) United States Patent
Yamamoto (10) Patent No.: US 7,079,236 B2
(45) Date of Patent: Jul. 18, 2006

(54) APPEARANCE INSPECTION MACHINE FOR FLAT TABLET

(75) Inventor: Taizo Yamamoto, Osaka (JP)

(73) Assignee: Nisshin Kasei Co., Ltd., Osaka (JP)

( * ) Notice: Subject to any disclaimer, the term of this patent is extended or adjusted under 35 U.S.C. 154(b) by 440 days.

(21) Appl. No.: 10/684,364

(22) Filed: Oct. 15, 2003

(65) Prior Publication Data

US 2004/0130709 A1    Jul. 8, 2004

(30) Foreign Application Priority Data

Oct. 16, 2002    (JP)    ............... 2002-301476

(51) Int. Cl.
G01N 21/00    (2006.01)
G01N 9/04    (2006.01)
(52) U.S. Cl. ............... 356/237.1; 250/223 R
(58) Field of Classification Search ... 356/237.1–237.6
See application file for complete search history.

(56) References Cited

U.S. PATENT DOCUMENTS 5,746,323 A    5/1998    Dragotta

FOREIGN PATENT DOCUMENTS

JP    01-320454 A    12/1989
JP    2000-097865 A    4/2000
JP    2001-033392 A    2/2001

Primary Examiner—Gregory J Toatley, Jr.
Assistant Examiner—Amanda Merlino
(74) Attorney, Agent, or Firm—Birch, Stewart, Kolasch & Birch, LLP (57) ABSTRACT

An appearance inspection apparatus is disclosed. A flat tablet (t) is placed in an uprightly erected posture on and between two adjacent ones of rollers (12) which form a roller belt (1), and is transported by the roller belt (1). During the transportation, a front surface image and a reverse surface image of the flat tablet (t) are fetched. Further, the two rollers (12) on which the flat tablet (t) is held are rotated by a rotatable roller (4) disposed on the lower side of the roller belt (1) to rotate the flat tablet (t). An image of the flat tablet (t) transported while being rotated in the uprightly erected posture is picked up from above to fetch an image of the overall circumference of the side face of the flat tablet (t).

6 Claims, 8 Drawing Sheets

APPEARANCE INSPECTION MACHINE FOR FLAT TABLET

This nonprovisional application claims priority under 35 U.S.C. § 119(a) on Patent Application No. 2002-301476 filed in JAPAN on Oct. 16, 2002, which is herein incorporated by reference.

BACKGROUND OF THE INVENTION

The present invention relates an appearance inspection apparatus for a flat tablet which picks up and fetches an image of the front surface, the reverse surface and the overall side face of a flat tablet, processes the thus fetched images to detect whether or not the flat tablet has an unacceptable appearance, and separately recovers unacceptable tablets having an unacceptable appearance and acceptable tablets having no unacceptable appearance.

Conventionally, an appearance inspection for inspecting whether or not a tablet suffers from a defect such as sticking of a foreign article or soiling to the tablet, deformation of the tablet such as a cut or a crack, or a defective print is automatically performed using an appearance inspection machine.

Conventionally, when an appearance inspection machine is used to automatically inspect a pharmaceutical tablet having a flattened shape (hereinafter referred to simply as "flat tablet"), the following method is generally used. In particular, flat tablets supplied at random are aligned and transported in a predetermined form. Then, during the transportation, the posture of each of the flat tablets is successively changed to an uprightly erected posture having a diametrical direction thereof directed in the vertical direction, a horizontally lying posture wherein the thickness-wise direction of the flat tablet is directed in the vertical direction and another horizontally lying posture wherein the front and reverse surfaces are directed reversely in the vertical direction. Every time each of the flat tablets assumes a different one of the postures, an image of the flat tablet is picked up. Consequently, a front surface image, a reverse surface image and a side face image of each of the flat tablets are fetched, and the thus fetched images are processed to detect whether or not the flat tablet has an appearance defect. It is to be noted that, although ordinary flat tablets do not specifically have a front surface and a reverse surface, in the present specification, the surface of a tablet whose image is picked up first is referred to as "front surface" while the other surface of the tablet whose image is picked up later is referred to as "reverse surface".

Conventionally, as one of such appearance inspection machines of the type described, the following apparatus inspection machine is known (refer to, for example, Japanese Patent Laid-Open No. 2001-33392). In particular, a plurality of transport drums are disposed such that the outer circumferential faces thereof are positioned close to each other, and flat tablets are held on the outer circumferential faces of the transport drums and transported successively by the drums while successively being delivered between the drums. During the transportation, such posture changes of each flat tablet as described above are performed to successively pick up images of the tablet in an upright posture, a horizontally lying posture and another horizontally lying posture with the front and reverse surfaces reversed.

However, the apparatus which is configured such that the posture changes of each flat tablet are performed while it is transferred between a plurality of transport drums to fetch images of the flat tablet in various postures in this manner is disadvantageous in that the transport path becomes extremely complicated inevitably and much advanced control is required for the speeds of rotation and synchronism adjustment and so forth of the drums, resulting in complication of the apparatus.

Further, a delivering operation between transport drums results in application of a high load to a tablet, and therefore, a cut or a crack is liable to occur with the tablet. In this instance, occurrence of a cut or a crack not only makes the tablet an unacceptable tablet, but causes sticking of a fraction of powder produced as a result of such cut or crack to another normal tablet. Therefore, there is the possibility that the normal tablet may be detected as an unacceptable product in error.

SUMMARY OF THE INVENTION

It is an object of the present invention to provide an appearance inspection apparatus for a flat tablet wherein a flat tablet is transported along a simple transport path and images of the front surface, the reverse surface and a side face of each flat tablet can be picked up with certainty with a comparatively simple mechanism to perform a good appearance inspection without applying an excessively high load to the flat tablet.

In order to attain the object described above, according to the first invention, there is provided an appearance inspection apparatus for a flat tablet which picks up and fetches images of a front surface, a reverse surface and an overall side face of a circular flat tablet, processes the fetched images to detect whether or not the flat tablet has a defective appearance, and separately recovers unacceptable flat tablets having a defective appearance and acceptable flat tablets having a non-defective appearance, including a roller belt having a plurality of rollers connected for rotation in a bridging manner between a pair of endless sprocket chains and being circulated at a predetermined speed, a tablet supplying section for supplying any of the flat tablets in an uprightly erected posture with a diametrical direction of the flat tablets directed in an upward and downward direction onto the roller belt, a guide path formed from and between a pair of guide walls disposed in a spaced relationship by a predetermined distance from each other in the proximity of an upper face of the roller belt on the downstream side in the circulation direction of the roller belt with respect to the tablet supplying section, a front surface image pickup apparatus for picking up an image of the flat tablet placed in the uprightly erected posture on and transported by the roller belt to fetch a front surface image of the flat tablet, a reverse surface image pickup apparatus for picking up an image of the flat tablet placed in the uprightly erected posture on and transported by the roller belt to fetch a reverse surface image of the flat tablet, a side face image pickup apparatus for picking up an image of the flat tablet placed in the uprightly erected posture on and transported by the roller belt to fetch an image of an overall periphery of a side face of the flat tablet, and a rotatable roller disposed in contact with a lower face of the roller belt at the position at which image pickup of the side face of the flat tablet is performed by the side face image pickup apparatus and rotatable at a predetermined speed to rotate those of the rollers of the roller belt with which the rotatable roller contacts, and wherein a flat tablet supplied from the tablet supplying section is held in an uprightly erected posture between adjacent ones of the rollers of the roller belt so that the flat tablet is transported in and along the guide path while keeping the uprightly erected posture, and while the flat tablet is transported, a front surface image of the flat tablet is picked up from one side in a direction perpendicular to the transport direction by the front surface image pickup apparatus whereas a reverse surface image of the flat tablet is picked up from the opposite side in the direction perpendicular to the transport direction by the reverse surface image pickup apparatus and besides an image of the flat tablet is picked up from above by the side face image pickup apparatus while the flat tablet is rotated on the rollers of the roller belt rotated by the rotatable roller to fetch an image of the overall periphery of the side face of the flat tablet.

In short, the appearance inspection apparatus is configured such that a flat tablet is placed in an uprightly erected posture onto and transported by the roller belt, and during the transportation, front surface, reverse surface and side face images of the tablet are fetched. In this instance, according to the present invention, the flat tablet is placed between two adjacent ones of the rollers which form the roller belt and is transported while the uprightly erected state of the flat tablet is kept by the guide path. Consequently, the flat tablet can be transported in the stable uprightly erected posture. Further, according to the present invention, images of the opposite front and reverse surfaces of the flat tablet being transported in the uprightly erected posture in this manner are picked up and fetched by the front surface image pickup apparatus and the reverse surface image pickup apparatus, respectively. Further, the two rollers on which the flat tablet is held are rotated by the rotatable roller disposed on the lower side of the roller belt to rotate the flat tablet at a predetermined speed in a fixed direction. Then, an image of the flat tablet being transported in the uprightly erected state while being rotated around its axis is picked up from above by the side face image pickup apparatus to fetch an image of the overall circumference of the side face of the flat tablet.

In this manner, in the appearance inspection apparatus, a flat tablet is placed on the roller belt and transported in an uprightly erected posture by the roller belt, and during the transportation, images of the opposite front and reverse surfaces and an image of the overall circumference of the side face of the flat tablet are fetched. Thus, a flat tablet can be transported along the linear, very simple transport path and front and reverse surface images and a side face image of the flat tablet can be fetched with certainty with a simple mechanism without requiring a cumbersome posture changing operation or delivering operation. Consequently, a good appearance inspection can be performed without applying an excessive load to the flat tablet.

Accordingly, an appearance inspection of a flat tablet of an object of inspection can be performed without applying an excessively high load to the flat tablet, and a good appearance inspection can be performed without causing the flat tablet to suffer from a break such as a crack or a cut. Further, since only the roller belt is used as a transport mechanism and a cumbersome posture changing operation or delivering operation is not required, a highly accurate appearance inspection can be performed by a comparatively simple mechanism without requiring such a complicated driving mechanism or control mechanism as is used wherein a plurality of transport drums are used.

Here, in the appearance inspection apparatus, the rollers which form the roller belt are rotated by the rotatable roller disposed on the lower side of the roller belt to rotate the flat tablet held on the rollers to fetch an image of the overall circumference of the side face of the flat tablet as described above. Therefore, where the flat tablet has a non-circular shape such as an elliptic shape or an elongated elliptic shape, it cannot be rotated readily around its axis, and an image of the overall circumference of the side face of the flat tablet cannot be fetched well.

Therefore, in this instance, the appearance inspection apparatus may be configured in the following manner. In particular, a posture changing section and a second side face image pickup apparatus are provided on the guide path on the downstream side in the transport direction with respect to the position at which side face image pickup by the side face image pickup apparatus is performed. The posture changing section includes an inclined portion along which the guide path is inclined to one side and an increased width portion provided contiguously to the inclined portion and capable of placing the flat tablet in a horizontally lying posture with a thickness-wise direction of the flat tablet directed in an upward and downward direction onto the roller belt. The second side face image pickup apparatus picks up an image of the flat tablet after the posture change by the posture changing section. In the appearance inspection apparatus, an image of the flat tablet is picked up first from above by the first side face image pickup apparatus while the flat tablet is kept in an uprightly erected posture without being rotated to fetch an image of a half circumference portion of the side face of the flat tablet. Then, the posture of the flat tablet is changed from the uprightly erected posture into a horizontally lying posture by the posture changing section. Thereafter, an image of the flat tablet is picked up by the second side face image pickup apparatus to fetch an image of the remaining half periphery portion of the side face of the flat tablet.

In this instance, the posture change from the uprightly erected posture to the horizontally lying posture by the posture changing section is performed such that, while the flat tablet is transported linearly in and along the guide path, the flat tablet in the uprightly erected posture is gradually inclined to the horizontally lying posture by the inclined portion of the path which is gradually inclined to one side. Therefore, the posture change can be performed smoothly without substantially applying a load to the flat tablet, and consequently, the flat tablet is not damaged at all.

According to the second invention, there is provided an appearance inspection apparatus for a flat tablet which picks up and fetches images of a front surface, a reverse surface and an overall side face of a non-circular flat tablet such as an elliptic flat tablet or an elongated elliptic flat tablet, processes the fetched images to detect whether or not the flat tablet has a defective appearance, and separately recovers unacceptable flat tablets having a defective appearance and acceptable flat tablets having a non-defective appearance, including a roller belt having a plurality of rollers connected for rotation in a bridging manner between a pair of endless sprocket chains and being circulated at a predetermined speed, a tablet supplying section for supplying any of the flat tablets in an uprightly erected posture with a diametrical direction of the flat tablets directed in an upward and downward direction onto the roller belt, a guide path formed from and between a pair of guide walls disposed in a spaced relationship by a predetermined distance from each other in the proximity of an upper face of the roller belt on the downstream side in the circulation direction of the roller belt with respect to the tablet supplying section, a front surface image pickup apparatus for picking up an image of the flat tablet placed in the uprightly erected posture on and transported by the roller belt to fetch a front surface image of the flat tablet, a reverse surface image pickup apparatus for picking up an image of the flat tablet placed in the uprightly erected posture on and transported by the roller belt to fetch a reverse surface image of the flat tablet, a first side face image pickup apparatus for picking up an image of a half periphery portion of a side face of the flat tablet placed in the uprightly erected posture on and transported by the roller belt to fetch an image of an overall periphery of a side face of the flat tablet, a posture changing section provided on the guide path on the downstream side in the transport direction with respect to the position at which side face image pickup by the first side face image pickup apparatus is performed and having an inclined portion along which the guide path is gradually inclined to one side and an increased width portion provided contiguously to the inclined portion and capable of placing the flat tablet in a horizontally lying posture with a thickness-wise direction of the flat tablet directed in an upward and downward direction onto the roller belt, and a second side face image pickup apparatus for picking up an image of the flat tablet transported in the horizontally lying posture after the posture change by the posture changing section to fetch an image of the remaining half periphery portion of the side face of the flat tablet, and wherein a flat tablet supplied from the tablet supplying section is held in an uprightly erected posture between adjacent ones of the rollers of the roller belt so that the flat tablet is transported in and along the guide path while keeping the uprightly erected posture, and while the flat tablet is transported, a front surface image of the flat tablet is picked up from one side in a direction perpendicular to the transport direction by the front surface image pickup apparatus whereas a reverse surface image of the flat tablet is picked up from the opposite side in the direction perpendicular to the transport direction by the reverse surface image pickup apparatus and besides an image of a half periphery portion of a side face of the flat tablet is picked up from above by the first side face image pickup apparatus, whereafter an image of the flat tablet after the posture of the flat tablet is changed into a horizontally lying posture by the posture changing section from the one side in the direction perpendicular to the transport direction by the second side face image pickup apparatus to fetch an image of the remaining half periphery portion of the side face of the flat tablet.

DETAILED DESCRIPTION OF THE INVENTION

In the following, the present invention is described in more detail in connection with preferred embodiments thereof.

Figure 1:
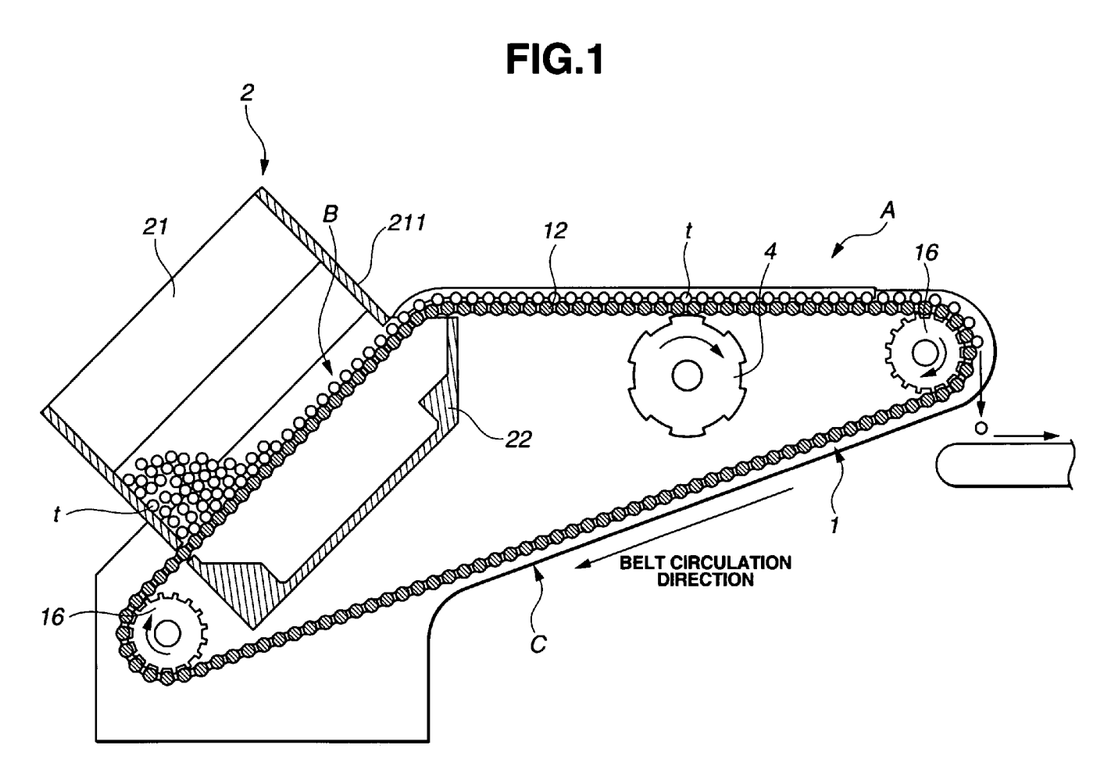
FIG. 1 is a schematic view showing an appearance inspection apparatus for a flat tablet according to an embodiment of the present invention.
Figure 2:
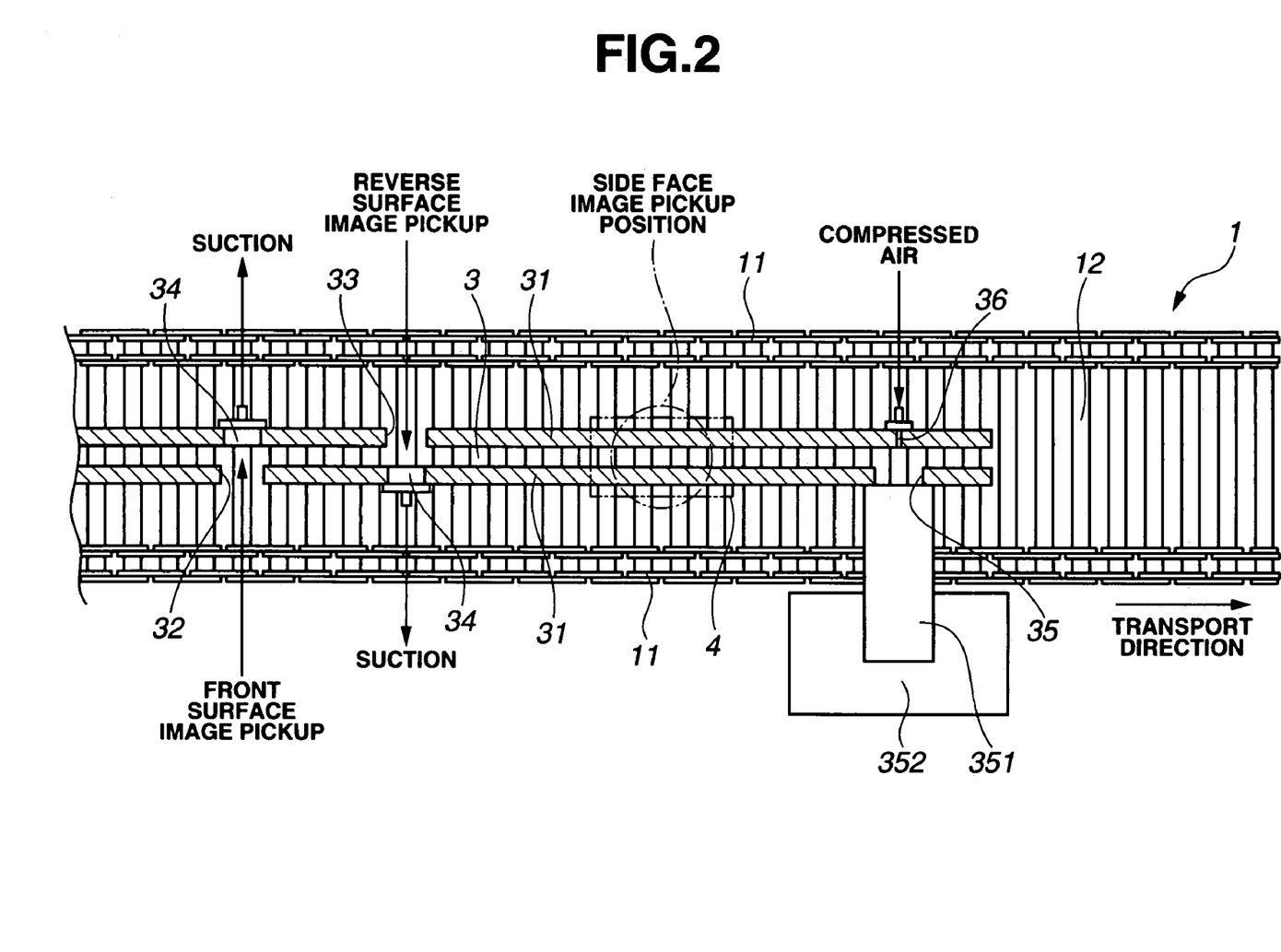
FIG. 2 is a schematic plan view, partly omitted, showing a transport mechanism section of the appearance inspection apparatus.

FIGS. 1 and 2 show an appearance inspection apparatus for a flat tablet according to an embodiment of the present invention. Referring to FIGS. 1 and 2, the appearance inspection apparatus shown picks up and fetches images of the front surface, the reverse surface and an overall side face of a circular flat tablet, processes the thus fetched images to detect whether or not the tablet has an unacceptable appearance and recovers such flat tablets separately as unacceptable tablets having an unacceptable appearance and acceptable tablets having no unacceptable appearance.

Reference numeral 1 in FIGS. 1 and 2 denote a roller belt for receiving and transporting flat tablet "t" of an object of inspection on an upper face thereof. Referring particularly to FIG. 2, the roller belt 1 includes a pair of endless sprocket chains 11, 11 disposed in parallel to each other, and a large number of rollers 12 connected in an equally spaced relationship from each other to the endless sprocket chains 11, 11 such that they bridge the endless sprocket chains 11, 11.

Figure 3:
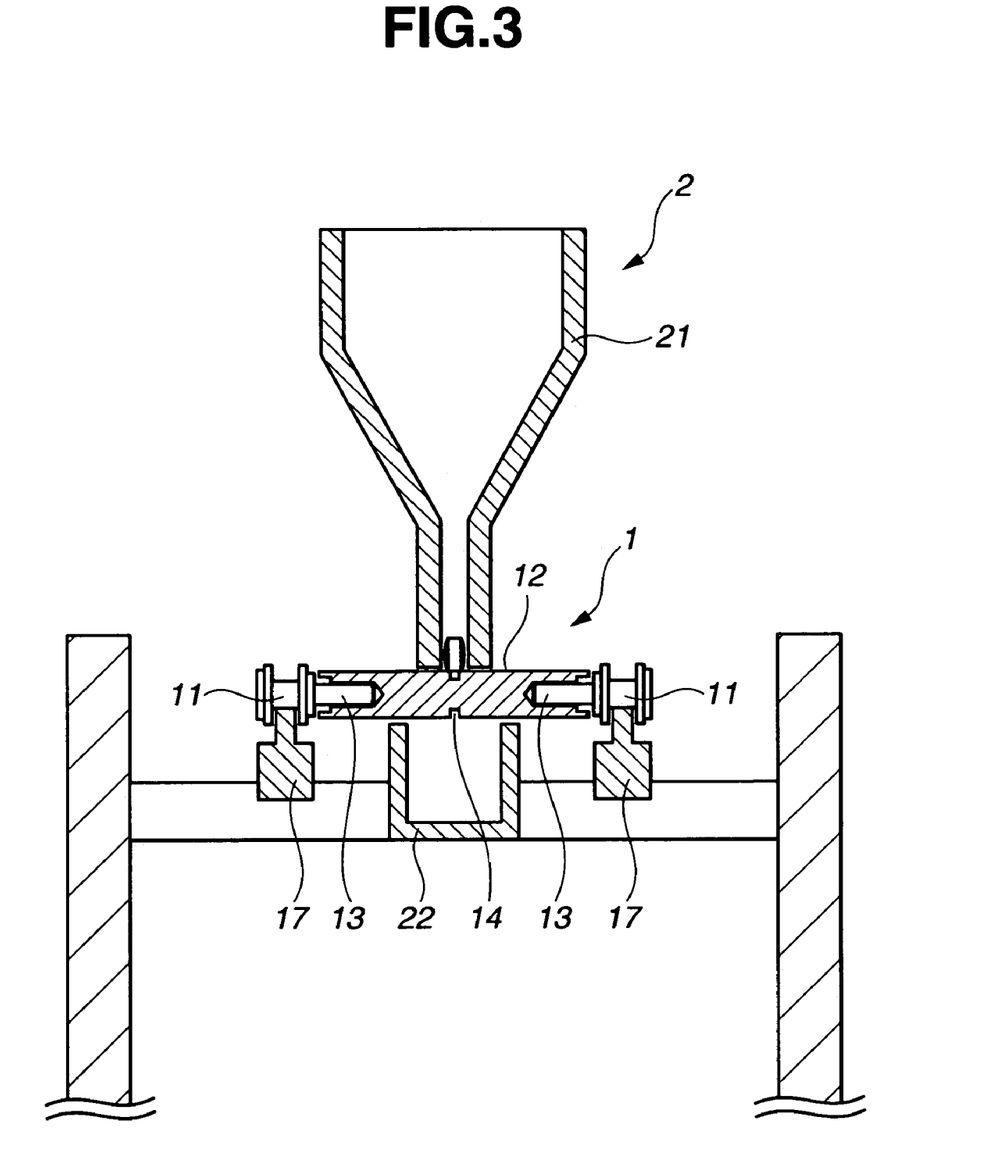
FIG. 3 is a schematic sectional view showing a tablet supplying section of the appearance inspection apparatus.
Figure 4:
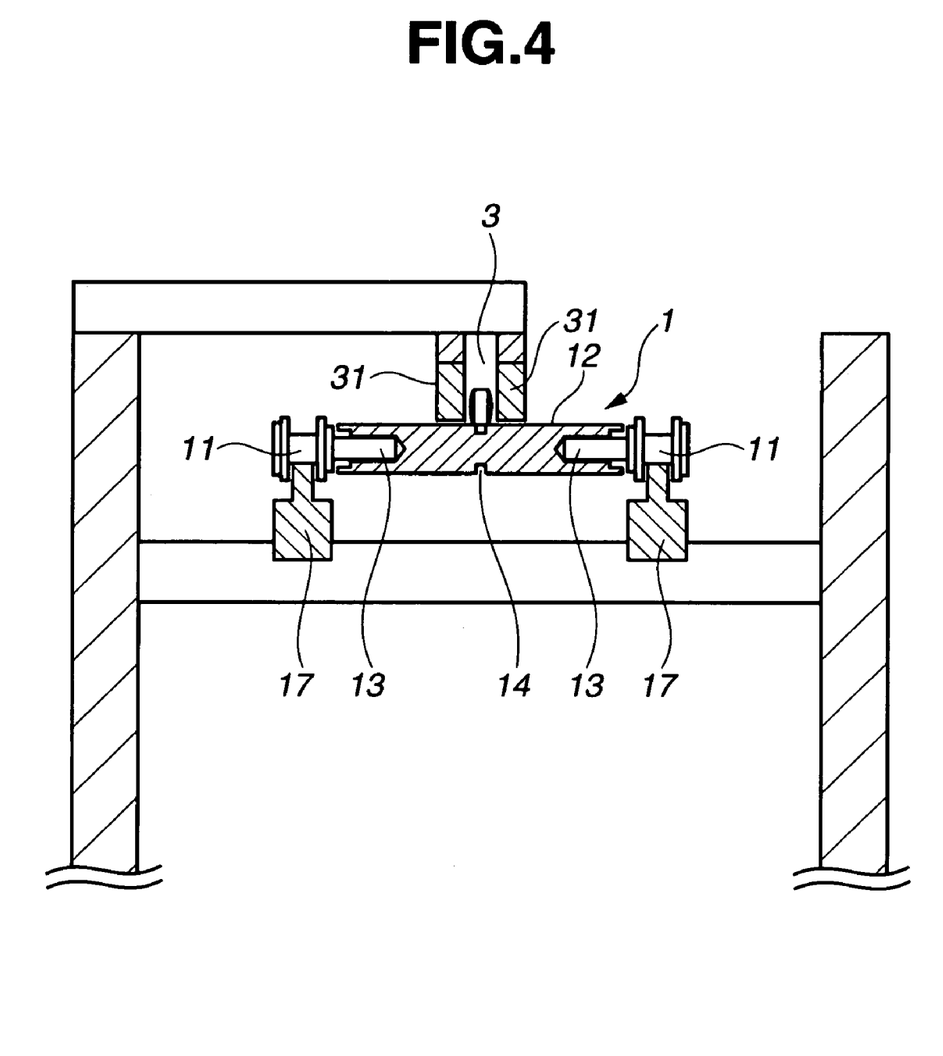
FIG. 4 is a schematic sectional view showing a transport section of the appearance inspection apparatus.
Figure 5:
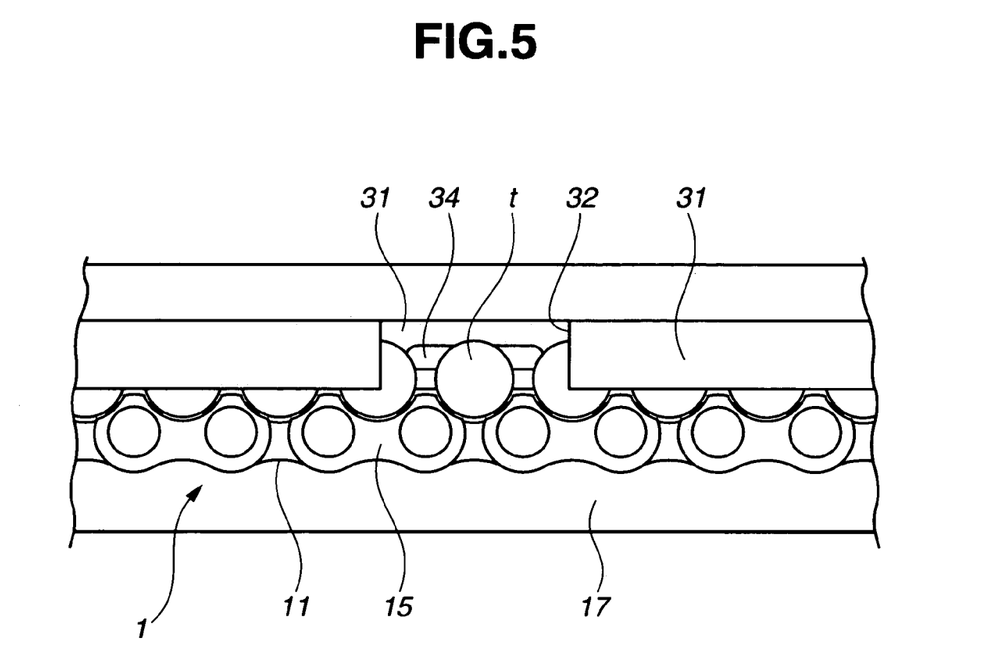
FIG. 5 is a partial enlarged view showing a front surface image pickup position of the appearance inspection apparatus.
Figure 6:
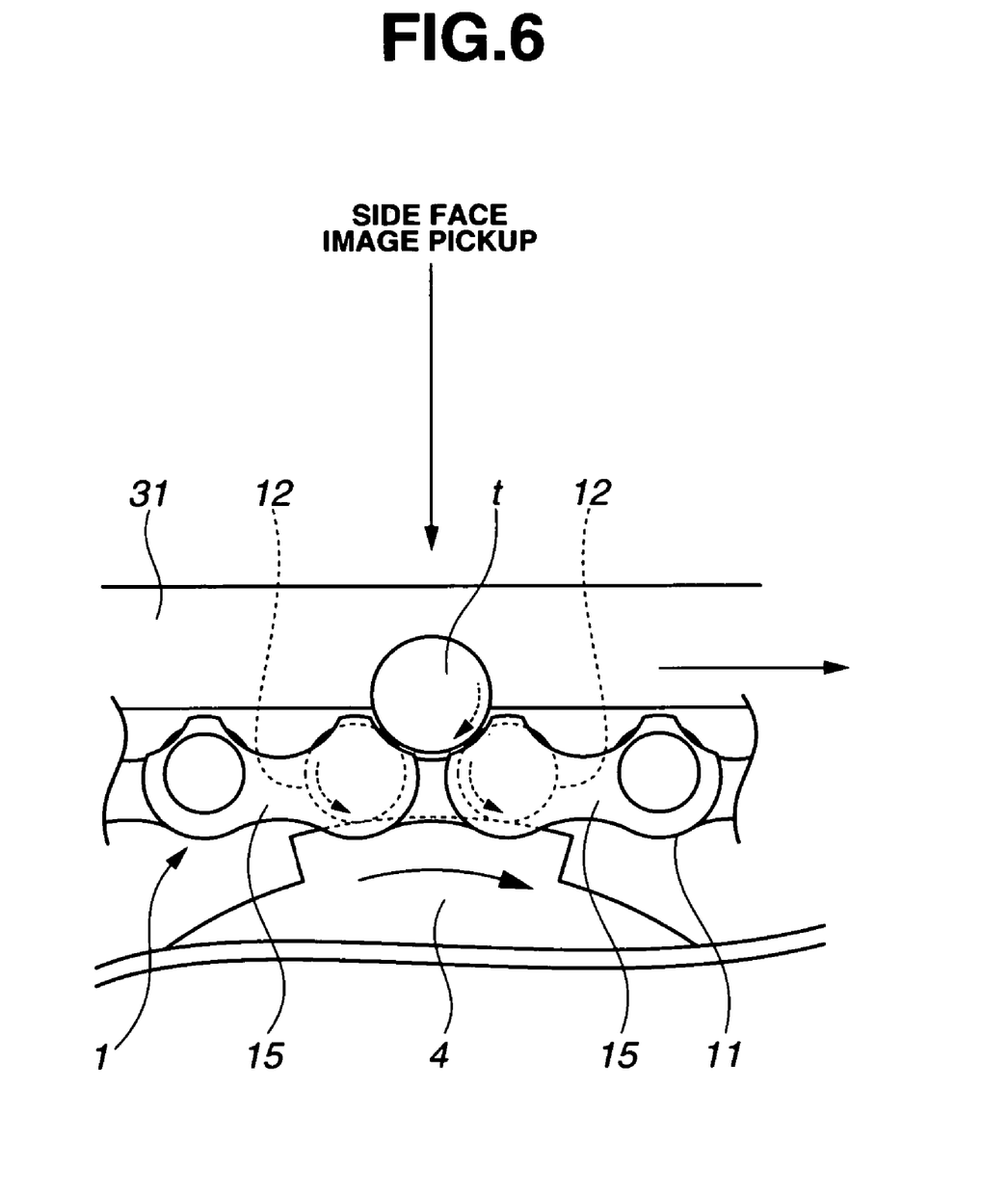
FIG. 6 is a partial enlarged view showing a side face image pickup position of the appearance inspection apparatus.

In this instance, as shown in FIGS. 3 and 4, each of the rollers 12 is mounted for rotation by a pair of support shafts 13, 13 individually provided in a projecting manner on the endless sprocket chains 11, 11 and has a ring-shaped suction groove 14 formed along a circumferential direction at a central portion in the longitudinal direction on an outer circumferential face thereof. The suction groove 14 has a width smaller than the thickness of the flat tablet "t" of an object of inspection. Further, as seen in FIGS. 5 and 6, each of side plates 15 which compose the sprocket chains 11 is arcuately cut away between a pair of rollers 12 such that the entire front and rear surfaces of the flat tablet "t" placed between the rollers 12 can be visually confirmed from sideward.

As shown in FIG. 1, the roller belt 1 is disposed in a triangularly shape including a transport portion A for moving horizontally, a supply portion B for moving obliquely upward, and a circulation section C for moving obliquely downward, and is driven to circulate in the clockwise direction in FIG. 1 by sprocket wheels 16. In this instance, in each of the transport portion A and the supply portion B, a pair of guide rails 17, 17 are disposed as seen in FIGS. 3 and 4 such that the sprocket chains 11, 11 may stably move along the guide rails 17, 17.

In the figures, reference numeral 2 denotes a tablet supplying section for supplying flat tablets "t" onto the roller belt 1. The tablet supplying section 2 includes a hopper 21 disposed above the roller belt 1 in the supply portion B, and a suction chamber 22 disposed on the lower face side of the roller belt 1.

As shown in FIG. 3, the hopper 21 has a box-shaped configuration whose upper and lower ends are opened and is formed such that an intermediate portion thereof in the upward and downward direction has a width which gradually decreases downwardly and a portion over a predetermined range adjacent the lower end thereof has a predetermined small width. The lower end opening of the hopper 21 having the decreased width is positioned in the proximity above the upper face of the roller belt 1. In this instance, the inner width of the lower opening end of the hopper 21 is a little greater than the thickness of the flat tablet "t" but is smaller than the diameter of the flat tablet "t". Thus, a flat tablet "t" is supplied onto the roller belt 1 in an uprightly erected posture with its diametrical direction directed in the upward and downward direction through the decreased width opening portion of the hopper 21. Further, a gap a little greater than the diameter of the flat tablet "t" is left between the lower end of a front end wall 211 (refer to FIG. 1) and the upper face of the roller belt 1 such that the flat tablet "t" in an upright posture is permitted to be transmitted through the gap.

It is to be noted that fine vibration may be applied to the hopper 21 so that the entrance of the decreased width portion of the hopper 21 may not be choked with tablets, or a suitable diaphragm or vibrator may be disposed in the hopper 21 to prevent choking with tablets.

Referring to FIGS. 1 and 3, the suction chamber 22 is disposed on the lower side of the roller belt 1 in a corresponding relationship to the lower end opening of the hopper 21. The inside of the suction chamber 22 is held in a decompressed state so that the flat tablets "t" on the roller belt 1 may be attracted to the roller belt 1 through the suction grooves 14 formed on the rollers 12 which compose the roller belt 1.

Referring to FIG. 2, a linear guide path 3 is disposed along a transport direction at a central portion in the widthwise direction of the roller belt 1 on the roller belt 1 in the transport portion A.

Referring to FIGS. 2 and 4, the guide path 3 is formed by and between a pair of guide walls 31, 31 disposed in the proximity above the roller belt 1 in a spaced relationship from each other by a predetermined distance. In this instance, the width of the guide path 3 is a little greater than the thickness of the flat tablet "t" but is smaller than the diameter of the flat tablet "t" such that a flat tablet "t" placed on the roller belt 1 may be transported in an uprightly erected posture in and along the guide path 3.

Referring to FIG. 2, a front surface image pickup window 32 and a reverse surface image pickup window 33 are formed successively along the transport direction in first and second ones of the guide walls 31, respectively. A front surface image pickup apparatus and a reverse face image pickup apparatus both not shown pick up images of a flat tablet "t" through the image pickup windows 32 and 33 to fetch a front surface image and a reverse surface image, respectively. In this instance, a suction slit 34 is formed in the first guide wall 31 which opposes to the front surface image pickup window 32 as seen in FIG. 5 such that a flat tablet "t" is sucked suitably through the suction slit 34 to keep the flat tablet "t" during image pickup in an uprightly erected posture with certainty. A similar structure is provided also for the reverse surface image pickup window 33.

Further, a side face image pickup apparatus (not shown) is disposed above the guide path 3 at a predetermined position (the side face image pickup position shown in FIG. 2) on the downstream side in the transport direction with respect to the reverse surface image pickup position at which the reverse surface image pickup window 33 is formed. The side face image pickup apparatus picks up an image of a flat tablet "t" moving in an uprightly erected posture within the guide path 3 to fetch a side face image of the flat tablet "t".

In this instance, as seen in FIGS. 1 and 6, a rotatable roller 4 which rotates at a predetermined speed is disposed on the lower side of the roller belt 1 at the side face image pickup position such that an outer peripheral face thereof contacts with some of the rollers 12 of the roller belt 1. By the rotation of the rotatable roller 4, the rollers 12 of the roller belt 1 are rotated at the side face image pickup position, whereupon a flat tablet "t" placed on the rollers 12 rotates around an axis thereof over 360 degrees or more at the side face image pickup position while keeping the uprightly erected posture. Consequently, an image of the side face of the flat tablet "t" is picked up over the overall circumference of the flat tablet "t", and as a result, an image of the side face over the overall circumference is fetched.

Here, the rotatable roller 4 rotates in the clockwise direction in FIG. 1 at a speed higher than the transport speed. Consequently, the rollers 12 of the roller belt 1 can be rotated stably at the side face image pickup position. Further, recesses are formed at predetermined intervals on the outer circumferential face of the rotatable roller 4 as seen in FIG. 1 so that the rotatable roller 4 can be stopped in a state wherein the outer circumferential face thereof does not contact with any of the rollers 12 of the roller belt 1.

Referring to FIG. 2, an unacceptable product discharging window 35 is formed in the first guide wall 31 on the downstream side in the transport direction with respect to the side face image pickup position. Meanwhile, a compressed air injection nozzle 36 is provided in the second guide wall 31 in an opposing relationship to the unacceptable product discharging window 35. When an unacceptable tablet having an unacceptable appearance is transported to the position where the unacceptable product discharging window 35 is formed, compressed air is jetted from the compressed air injection nozzle 36 to discharge the unacceptable tablet from the guide path 3 through the unacceptable product discharging window 35. In this instance, the unacceptable tablet discharged from the guide path 3 is recovered into an unacceptable product recovery can 352 through a discharging chute 351.

It is to be noted that an apparatus having a known configuration including a combination of a camera and an illumination apparatus can be used for the front surface image pickup apparatus, reverse surface image pickup apparatus and side face image pickup apparatus described above. The camera may be a two-dimensional camera or a one-dimensional camera.

The appearance inspection apparatus further includes an acceptance/rejection determination section not shown. The acceptance/rejection determination section processes a front surface image, a reverse surface image and a side face image fetched as described above to determine whether or not the tablet in question has an unacceptable appearance. Then, in response to a result of the determination, compressed air is jetted suitably from the compressed air injection nozzle 36 to selectively remove the thus determined unacceptable tablet from the guide path 3.

Now, operation of the appearance inspection apparatus is described.

When flat tablets "t" of an object of inspection are thrown into the hopper 21 of the supplying section 2 described hereinabove, the flat tablets "t" are successively supplied in an uprightly erected posture onto the roller belt 1 as described above by the action of the decreased width portion provided at the inclined portion and the lower end portion of the hopper 21. Each of the flat tablets "t" is held in a state wherein it extends between two adjacent ones of the rollers 12 of the roller belt 1 under a sucking action from the suction chamber 22. The flat tablet "t" is transported in this state by a circulating movement of the roller belt 1 such that it moves from the left side to the right side in FIGS. 1 and 2 within and along the guide path 3.

An image of the flat tablet "t" transported in this manner is picked up first from one side in a direction perpendicular to the transport direction through the front surface image pickup window 32 by the front surface image pickup apparatus. Then, another image of the flat tablet "t" is picked up from the opposite side in the direction perpendicular to the transport direction through the reverse surface image pickup window 33 by the reverse face image pickup apparatus. Thereafter, a further image of the flat tablet "t" is picked up from above by the side face image pickup apparatus while the flat tablet "t" rotates around its axis on the rollers 12 of the roller belt 1 which are rotated by the rotatable roller 4. Consequently, a front surface image, a reverse surface image and a side face image of the flat tablet "t" are fetched.

The images fetched in this manner are processed immediately by the acceptance/rejection determination section to perform determination of whether or not the flat tablet "t" is acceptable. If it is determined that the flat tablet "t" is not acceptable, then when the flat tablet "t" is transported to the position at which the unacceptable product discharging window 35 is formed, compressed air is jetted from the compressed air injection nozzle 36 as described above to discharge the flat tablet "t" from the guide path 3 so that the flat tablet "t" is recovered into the unacceptable product recovery can 352. On the other hand, if the flat tablet "t" is determined to be an acceptable product free from a defect in appearance, then it passes as it is by the position at which the unacceptable product discharging window 35 is formed and is then discharged from the appearance inspection apparatus and recovered.

In this manner, in the present appearance inspection apparatus, a flat tablet "t" is placed on the roller belt 1 and transported in an uprightly erected posture, and during the transportation, images of the opposite front and reverse surfaces and an image of an overall circumference of the side face of the flat tablet "t" are fetched. Thus, a flat tablet "t" can be transported along a linear, very simple transport path and front and reverse surface images and a side face image of the flat tablet "t" can be fetched with certainty with a simple mechanism without requiring a cumbersome posture changing operation or delivering operation. Consequently, a good appearance inspection can be performed without applying an excessive load to the flat tablet "t".

Accordingly, an appearance inspection of a flat tablet "t" of an object of inspection can be performed without applying an excessively high load to the flat tablet "t", and a good appearance inspection can be performed without causing the flat tablet "t" to suffer from a break such as a crack or a cut. Further, since only the roller belt 1 is used as a transport mechanism and a cumbersome posture changing operation or delivering operation is not required, a highly accurate appearance inspection can be performed by a comparatively simple mechanism without requiring such a complicated driving mechanism or control mechanism as is used wherein a plurality of transport drums are used.

Here, in the appearance inspection apparatus, the rollers 12 which form the roller belt 1 are rotated by the rotatable roller 4 disposed on the lower side of the roller belt 1 to rotate the flat tablet "t" held on the rollers 12 to fetch an image of the overall circumference of the side face of the flat tablet as described above. Therefore, where the flat tablet otherwise has a non-circular shape such as an elliptic shape or an elongated elliptic shape, it cannot be rotated readily around its axis, and an image of the overall circumference of the side face thereof cannot be fetched well.

Figure 7:
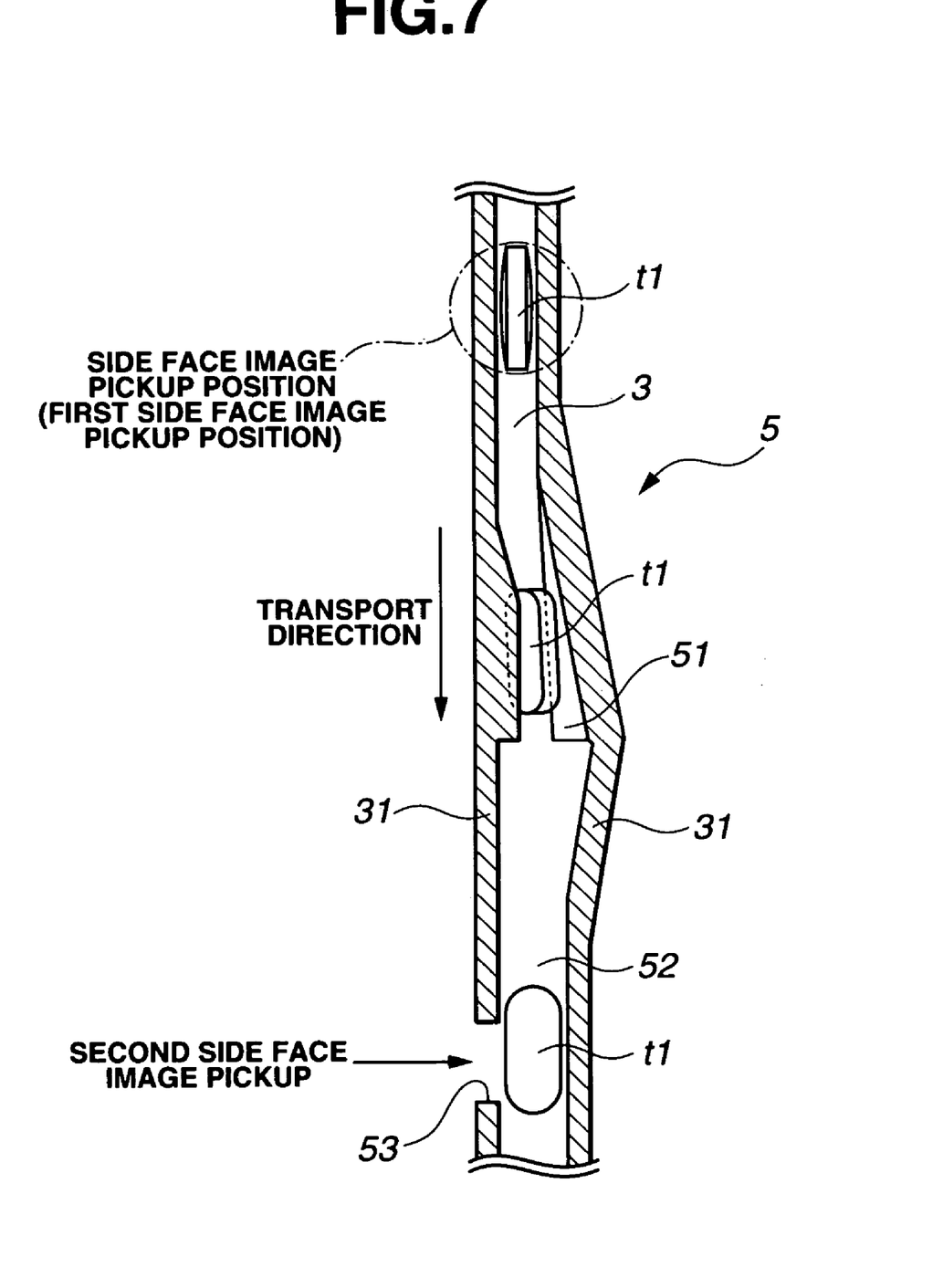
FIG. 7 is a schematic horizontal sectional view showing a posture changing section of an appearance inspection apparatus for a tablet according to another embodiment of the present invention.
Figure 8:
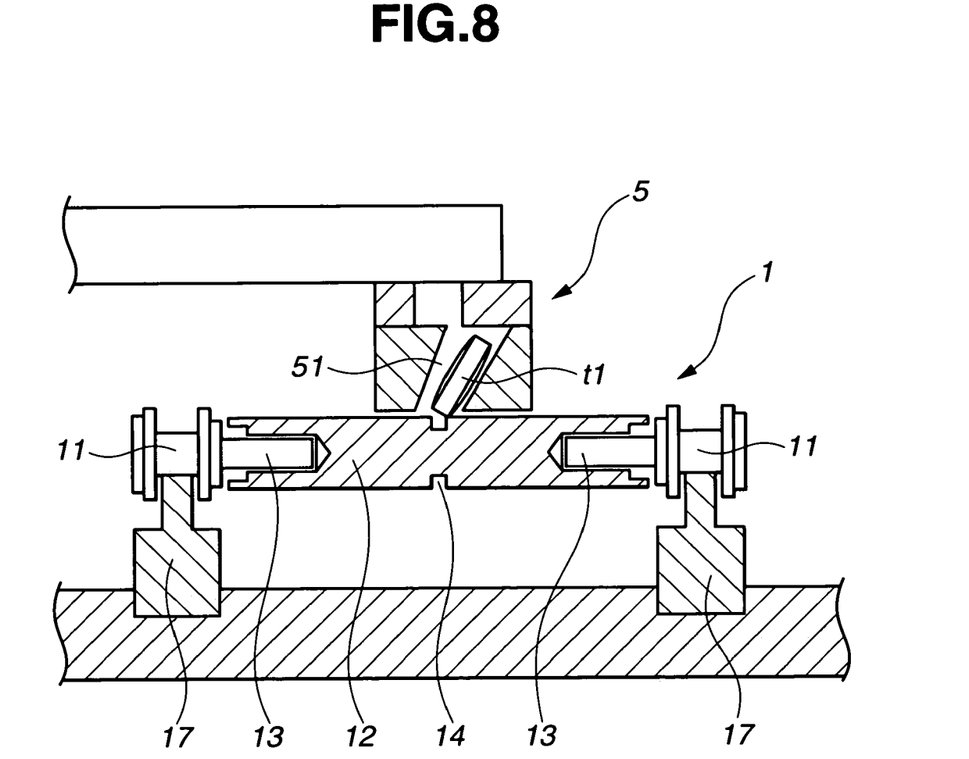
FIG. 8 is a schematic vertical sectional view showing the posture changing section.

Therefore, in order to perform an inspection of such a non-circular flat tablet as just mentioned, for example, the following countermeasure may be used. In particular, all or one of the guide walls 31, 31 are replaced, and a posture changing section 5 shown in FIGS. 7 and 8 is provided on the guide path 3 between the side face image pickup position and the position at which the unacceptable product discharging window 35 is formed. Further, a second side face image pickup apparatus (not shown) is disposed for picking up an image of a flat tablet t1 after the posture thereof is changed by the posture changing section 5.

Referring to FIGS. 7 and 8, the posture changing section 5 shown has a guide path 3 which includes an inclined portion 51 inclined gradually to one side, and an increased width portion 52 contiguous to the inclined portion 51 and capable of placing a non-circular (in FIG. 7, elongated elliptic) flat tablet t1 in a horizontally lying posture with the thickness-wise direction thereof directed in the vertical direction onto the roller belt 1. Further, a side face image pickup window 53 through which second side face image pickup can be performed is provided in the first guide wall 31 on the downstream side in the transport direction with respect to the posture changing section 5 as seen in FIG. 7.

In operation, the rotatable roller 4 is stopped in a position thereof in which its outer periphery does not contact with the rollers 12, and image pickup of the flat tablet t1 is performed from above by the first side face image pickup apparatus while the flat tablet t1 is kept in an uprightly erected posture and is not rotated around its axis to fetch an image of a half periphery of the side face of the flat tablet t1. Thereafter, the posture of the flat tablet t1 is changed from the uprightly erected posture to a horizontally lying posture by the posture changing section 5, and then an image of the remaining half periphery of the side face of the flat tablet t1 is fetched through the side face image pickup window 53 by the second side face image pickup apparatus.

In this instance, the posture change from the uprightly erected posture to the horizontally lying posture by the posture changing section 5 is performed such that, while the flat tablet t1 is transported linearly in and along the guide path 3, the flat tablet t1 in the uprightly erected posture is gradually inclined to the horizontally lying posture by the inclined portion 51 which is gradually inclined to one side. Therefore, the posture change can be performed smoothly without substantially applying a load to the flat tablet t1, and consequently, the flat tablet t1 is not damaged at all.

It is to be noted that the appearance inspection apparatus of the present invention is not limited to the embodiments described above, but the tablet supplying section, the unacceptable tablet discharging mechanism and so forth can be modified suitably. Also the remaining configuration can be modified in various forms without departing from the spirit and scope of the present invention.

As described above, with the appearance inspection apparatus of the present invention, a flat tablet is transported by a simple transport path, and front and reverse surface images and a side face image of the tablet can be fetched with certainty by a comparatively simple mechanism without requiring a cumbersome posture changing operation or delivering operation. Consequently, a good appearance inspection can be performed without applying an excessively high load to the tablet.

Japanese Patent Application No. 2002-301476 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An appearance inspection apparatus for a flat tablet which picks up and fetches images of a front surface, a reverse surface and an overall side face of a circular flat tablet, processes the fetched images to detect whether or not the flat tablet has a defective appearance, and separately recovers unacceptable flat tablets having a defective appearance and acceptable flat tablets having a non-defective appearance, comprising:

a roller belt including a plurality of rollers connected for rotation in a bridging manner between a pair of endless sprocket chains and being circulated at a predetermined speed;

a tablet supplying section for supplying any of the flat tablets in an uprightly erected posture with a diametrical direction of the flat tablets directed in an upward and downward direction onto said roller belt;

a guide path formed from and between a pair of guide walls disposed in a spaced relationship by a predetermined distance from each other in the proximity of an upper face of said roller belt on the downstream side in the circulation direction of said roller belt with respect to said tablet supplying section;

a front surface image pickup apparatus for picking up an image of the flat tablet placed in the uprightly erected posture on and transported by said roller belt to fetch a front surface image of the flat tablet;

a reverse surface image pickup apparatus for picking up an image of the flat tablet placed in the uprightly erected posture on and transported by said roller belt to fetch a reverse surface image of the flat tablet;

a side face image pickup apparatus for picking up an image of the flat tablet placed in the uprightly erected posture on and transported by said roller belt to fetch an image of an overall periphery of a side face of the flat tablet; and a rotatable roller disposed in contact with a lower face of said roller belt at the position at which image pickup of the side face of the flat tablet is performed by said side face image pickup apparatus and rotatable at a predetermined speed to rotate said rollers of said roller belt with which said rotatable roller contacts; and wherein a flat tablet supplied from said tablet supplying section is held in an uprightly erected posture between adjacent ones of said rollers of said roller belt so that the flat tablet is transported in and along said guide path while keeping the uprightly erected posture, and while the flat tablet is transported, a front surface image of the flat tablet is picked up from one side in a direction perpendicular to the transport direction by said front surface image pickup apparatus whereas a reverse surface image of the flat tablet is picked up from the opposite side in the direction perpendicular to the transport direction by said reverse surface image pickup apparatus and an image of the flat tablet is picked up from above by said side face image pickup apparatus while the flat tablet is rotated on the rollers of said roller belt rotated by said rotatable roller to fetch an image of the overall periphery of the side face of the flat tablet.

2. An appearance inspection apparatus for a flat tablet according to claim 1, wherein a ring-shaped suction groove is formed along a circumferential direction on each of said rollers of said roller belt such that, at least at a location at which a tablet is supplied onto said roller belt from said tablet supplying section, the tablet is sucked through the suction grooves of the adjacent rollers from the lower side of said roller belt so that the tablet is held between the rollers by the suction force.

3. An appearance inspection apparatus for a flat tablet according to claim 1 or 2, wherein a image pickup window is formed in one of said guide walls which define said guide path while a suction slit is formed in the other of said guide walls at each of the locations at which image pickup is performed by said front surface image pickup apparatus and said reverse surface image pickup apparatus such that a flat tablet is sucked through said suction slit to keep the uprightly erected posture of the flat tablet while an image of the flat tablet is picked up through said image pickup window by said front surface image pickup apparatus or said reverse surface image pickup apparatus.

4. An appearance inspection apparatus for a flat tablet which picks up and fetches images of a front surface, a reverse surface and an overall side face of a non-circular flat tablet such as an elliptic flat tablet or an elongated elliptic flat tablet, processes the fetched images to detect whether or not the flat tablet has a defective appearance, and separately recovers unacceptable flat tablets having a defective appearance and acceptable flat tablets having a non-defective appearance, comprising:

a roller belt including a plurality of rollers connected for rotation in a bridging manner between a pair of endless sprocket chains and being circulated at a predetermined speed;

a tablet supplying section for supplying any of the flat tablets in an uprightly erected posture with a diametrical direction of the flat tablets directed in an upward and downward direction onto said roller belt;

a guide path formed from and between a pair of guide walls disposed in a spaced relationship by a predetermined distance from each other in the proximity of an upper face of said roller belt on the downstream side in the circulation direction of said roller belt with respect to said tablet supplying section;

a front surface image pickup apparatus for picking up an image of the flat tablet placed in the uprightly erected posture on and transported by said roller belt to fetch a front surface image of the flat tablet;

a reverse surface image pickup apparatus for picking up an image of the flat tablet placed in the uprightly erected posture on and transported by said roller belt to fetch a reverse surface image of the flat tablet;

a first side face image pickup apparatus for picking up an image of a half periphery portion of a side face of the flat tablet placed in the uprightly erected posture on and transported by said roller belt to fetch an image of an overall periphery of a side face of the flat tablet;

a posture changing section provided on said guide path on the downstream side in the transport direction with respect to the position at which side face image pickup by said first side face image pickup apparatus is performed and including an inclined portion along which said guide path is gradually inclined to one side and an increased width portion provided contiguously to said inclined portion and capable of placing the flat tablet in a horizontally lying posture with a thickness-wise direction of the flat tablet directed in an upward and downward direction onto said roller belt; and a second side face image pickup apparatus for picking up an image of the flat tablet transported in the horizontally lying posture after the posture change by said posture changing section to fetch an image of the remaining half periphery portion of the side face of the flat tablet; and wherein a flat tablet supplied from said tablet supplying section is held in an uprightly erected posture between adjacent ones of said rollers of said roller belt so that the flat tablet is transported in and along said guide path while keeping the uprightly erected posture, and while the flat tablet is transported, a front surface image of the flat tablet is picked up from one side in a direction perpendicular to the transport direction by said front surface image pickup apparatus whereas a reverse surface image of the flat tablet is picked up from the opposite side in the direction perpendicular to the transport direction by said reverse surface image pickup apparatus and an image of a half periphery portion of a side face of the flat tablet is picked up from above by said first side face image pickup apparatus, whereafter an image of the flat tablet after the posture of the flat tablet is changed into a horizontally lying posture by said posture changing section from the one side in the direction perpendicular to the transport direction by said second side face image pickup apparatus to fetch an image of the remaining half periphery portion of the side face of the flat tablet.

5. An appearance inspection apparatus for a flat tablet according to claim 4, wherein a ring-shaped suction groove is formed along a circumferential direction on each of said rollers of said roller belt such that, at least at a location at which a tablet is supplied onto said roller belt from said tablet supplying section, the tablet is sucked through the suction grooves of the adjacent rollers from the lower side of said roller belt so that the tablet is held between the rollers by the suction force.

6. An appearance inspection apparatus for a flat tablet according to claim 4 or 5, wherein a image pickup window is formed in one of said guide walls which define said guide path while a suction slit is formed in the other of said guide walls at each of the locations at which image pickup is performed by said front surface image pickup apparatus and said reverse surface image pickup apparatus such that a flat tablet is sucked through said suction slit to keep the uprightly erected posture of the flat tablet while an image of the flat tablet is picked up through said image pickup window by said front surface image pickup apparatus or said reverse surface image pickup apparatus.

* * * * *